United States Patent
Drucker

[11] Patent Number: 5,964,777
[45] Date of Patent: Oct. 12, 1999

[54] SURGICAL CUTTING INSTRUMENT

[75] Inventor: Karen Drucker, Danville, N.H.

[73] Assignee: Smith & Nephew, Inc., Andover, Mass.

[21] Appl. No.: 08/988,739

[22] Filed: Dec. 11, 1997

[51] Int. Cl.$^6$ .................................................. A61B 17/14
[52] U.S. Cl. .................... 606/180; 606/167; 606/170; 606/171; 606/172; 604/22; 604/24
[58] Field of Search ............................ 606/180, 167–184; 604/22, 24

[56] References Cited

U.S. PATENT DOCUMENTS

| | | | |
|---|---|---|---|
| 4,203,444 | 5/1980 | Bonnell et al. | 604/22 |
| 4,274,414 | 6/1981 | Johnson et al. | 128/305 |
| 4,517,977 | 5/1985 | Frost | 128/305 |
| 4,598,710 | 7/1986 | Kleinberg et al. . | |
| 4,631,052 | 12/1986 | Kensey | 604/22 |
| 4,649,919 | 3/1987 | Thimsen et al. . | |
| 4,681,106 | 7/1987 | Kensey et al. | 128/305 |
| 4,834,729 | 5/1989 | Sjostrom | 128/318 |
| 4,842,578 | 6/1989 | Johnson et al. | 604/22 |
| 4,983,179 | 1/1991 | Sjostrom | 606/180 |
| 4,998,527 | 3/1991 | Meyer | 128/6 |
| 5,320,635 | 6/1994 | Smith | 606/180 |
| 5,510,070 | 4/1996 | Krause et al. | 264/156 |
| 5,601,583 | 2/1997 | Donahue et al. . | |
| 5,620,447 | 4/1997 | Smith et al. | 606/79 |

FOREIGN PATENT DOCUMENTS

| | | | |
|---|---|---|---|
| 38 28 478 | 8/1988 | Germany . | |
| 3828478 | 8/1988 | Germany | 606/180 |
| 61-265133 | 11/1986 | Japan . | |

OTHER PUBLICATIONS 4.0 mm Turbocutter Blade, No. 8018331 May 1996, tip outer, tip inner, tube assembly outer, tube assembly inner, (Drawings, 4 sheets).

Primary Examiner—Michael Buiz
Assistant Examiner—Lien Ngo
Attorney, Agent, or Firm—Fish & Richardson P.C.

[57] ABSTRACT

A surgical cutting instrument, disposed generally along a rotational axis, includes a member extending from a base. The member is rotatable to transmit torque from the base to a cutter carried at the distal end of the member. The cutter defines one cutting edge oriented in a right-handed direction, and another cutting edge oriented in a left-handed direction. The right-handed and left-handed cutting edges can be, e.g., defined by a symmetrical revolved surface, forward-swept, symmetrical, or separated by an uninterrupted circumferential band of material.

39 Claims, 4 Drawing Sheets

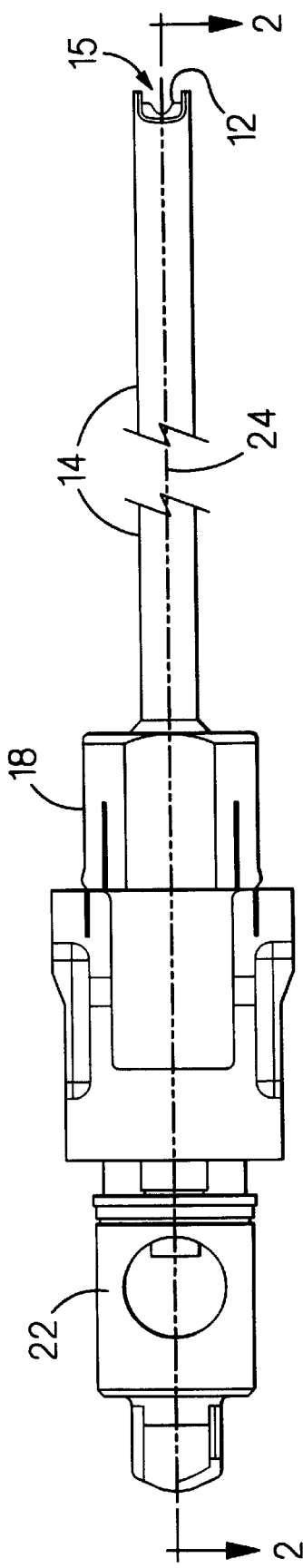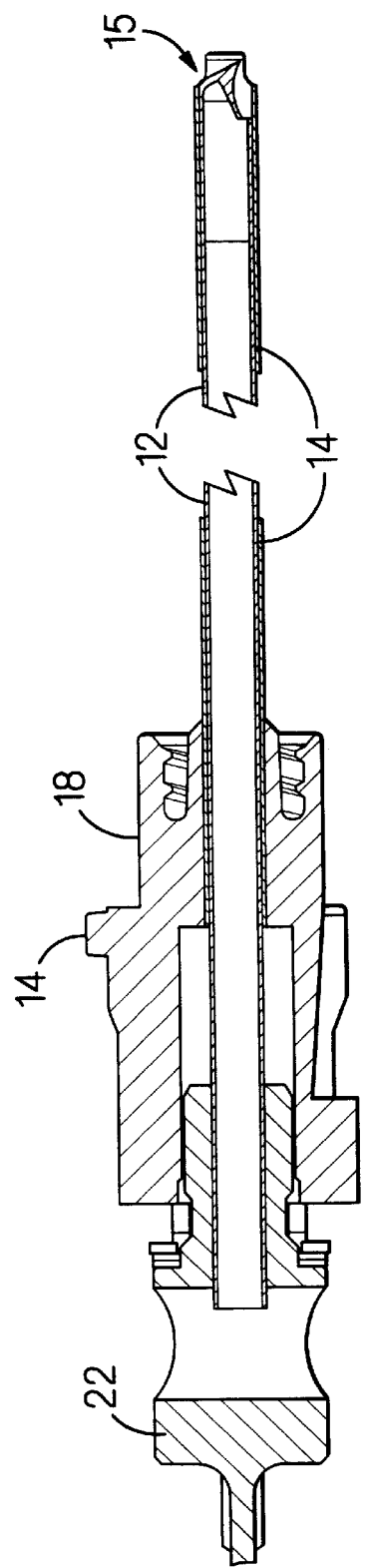

SURGICAL CUTTING INSTRUMENT

BACKGROUND OF THE INVENTION

This invention relates to surgical instruments, and in particular to powered arthroscopic surgical instruments.

Powered arthroscopic surgical instruments typically include a rigid, stationary outer tube within which an inner tube is rotated by a motor. A cutting implement is disposed on the distal end of the inner tube. Tissue is exposed to the cutting implement through an opening in the distal end of the outer tube, and tissue or bone fragments cut by the cutting implement are often drawn through the interior of the inner tube along with irrigating fluid by the use of suction applied at the proximal end of the instrument. Examples of such surgical instruments are described in U.S. Pat. Nos. 4,203,444, 4,274,414, 4,834,729, and 4,842,578, all of which are assigned to the present assignee, and all of which are incorporated herein by reference.

SUMMARY OF THE INVENTION

One aspect of the invention is a surgical cutting instrument in which a rotatable member transmits torque to a cutter carried at its distal end. The cutter has a cutting edge defined by a symmetrical revolved surface.

Among other advantages, as the member rotates, the edge defined by the symmetrical revolved surface can cut tissue during a surgical procedure, e.g., medium tissue such as cartilage.

Preferred embodiments of this aspect include the following features.

The symmetrical revolved surface defines two cutting edges, one oriented in a right-handed direction and the other oriented in a left-handed direction. Both edges are forward-swept, and symmetrical with respect to one another about a plane of symmetry. The symmetrical right-handed and left-handed cutting edges enable the instrument to cut, e.g., tissue as the member rotates either clockwise or counterclockwise. By selecting the appropriate direction of rotation, the cutter can thus be moved tangentially in either direction across the surface of the material being cut. For strength during cutting, an uninterrupted circumferential band extends between the two edges. The distal end of the cutter defines a generally planar area that intersects the cutting edges at distal points. The planar area lies at a 30° to 90° (e.g., 65°) to the longitudinal axis of the cutter, and includes a notch.

A relatively rigid hollow outer member terminates at its distal end in a pair of longitudinally extending tabs. Each tab defines a pair of right-handed and left-handed cutting edges, which edges define a pair of openings extending along the longitudinal axis of the outer member. The distal end of the second member is substantially entirely open to expose the distal end of the cutter.

In another aspect of the invention, a rotatable member of a surgical cutting instrument transmits torque to a cutter carried at its distal end. The distal end of the cutter defines a generally planar area that lies at an acute angle to the axis of the rotatable member, and that intersects right-handed and left-handed cutting edges of the cutter at respective right and left points.

Among other advantages, the generally planar area intersects the edges to form a point that facilitates the initiation of the cut. The angle at which the planar area lies to the axis of rotation of the instrument (e.g., 30° to 75°, preferably 65°) determines the "pointedness" of these cut-initiating points. Moreover, the edge of the generally planar surface forms an additional cutting edge that extends between the right-handed and left-handed cutting edges of the cutter.

In another aspect of the invention, a rotatable member of a surgical cutting instrument transmits torque to a cutter carried at its distal end. The cutter has forward-swept right-handed and left-handed cutting edges. The rotatable member is coaxially disposed with and rotates within a relatively rigid hollow outer member. The distal end of the outer member is substantially entirely open to expose the distal end of the cutter Among other advantages, the substantially entirely open distal end of the outer member permits axial boring, or end-on cutting, by the forward-swept cutting edges.

Other features and advantages of the invention will be apparent from the description of the preferred embodiments, and from the claims.

BRIEF DESCRIPTION OF THE DRAWINGS

FIG. 1 is a front view of a surgical cutting instrument.

FIG. 2 is a sectional view of the surgical cutting instrument taken through line 2—2 in FIG. 1.

DESCRIPTION OF THE PREFERRED EMBODIMENTS

Referring to FIGS. 1 and 2, a surgical cutting instrument 10 suitable for cutting tissue, particularly medium tissue such as cartilage, during, e.g, arthroscopic knee surgery, includes an inner member 12 and an outer member 14. Tissue is cut at the distal end of the surgical cutting instrument 10 by a cutting implement 15.

Figure 3:
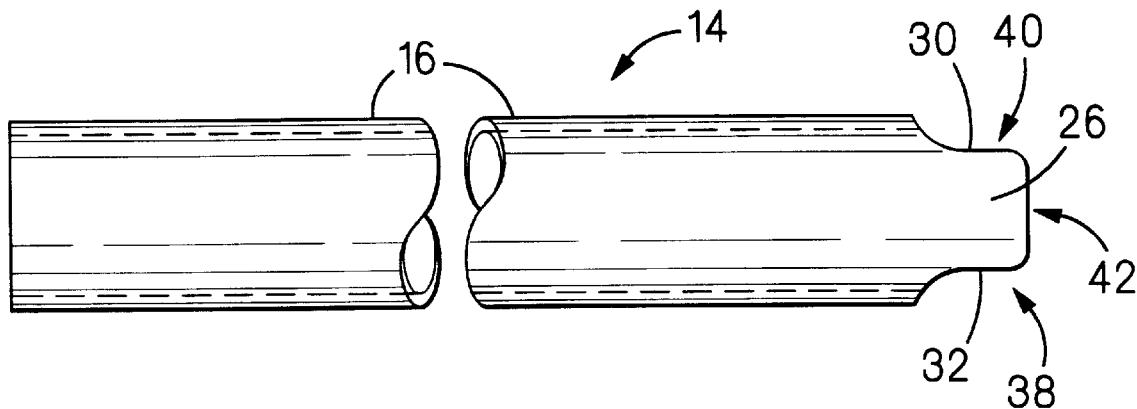
FIG. 3 is a side view of an outer tube of the surgical cutting instrument shown in FIG. 1.
Figure 4:
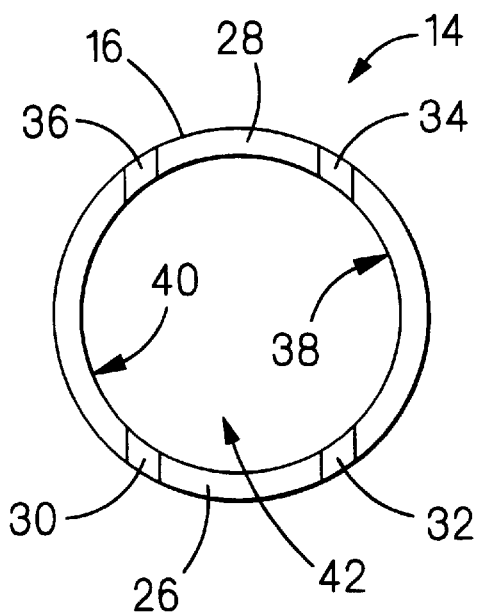
FIG. 4 is a distal end view of the outer tube shown in FIG. 3.

Referring also to FIGS. 3 and 4, the outer member 14 includes a hollow outer tube 16, the proximal end of which is connected to a base 18. The outer tube 16 has a length of, e.g., 146.256 mm (5.704"), an outer diameter of 4.231 mm (0.165"), and an inner diameter of 3.590 mm–3.615 mm (0.140'–0.141"). The inner diameter of the outer tube 16 is constant along its length. The distal end of the outer tube 16 includes a pair of tabs 26, 28. The tabs 26, 28 extend longitudinally and are located along the circumference of the outer tube 16. Each one of the tabs 26, 28 defines a right-handed cutting edge 30, 34 and a left-handed cutting edge 32, 36.

The tabs 26, 28 define three openings in the distal end of the outer tube 16: two side-facing openings 38, 40 and one distal-end opening 42. The tabs 26, 28 are configured so that the openings 38, 40, and 42 form one contiguous open area. Each of the tabs 26, 28 is, e.g., 2.564 mm (0.100") long with corners radiused to 0.385 mm (0.015"). The side-facing openings 38, 40 are substantially semicircular with a radius of 1.282 mm (0.050").

Figure 5:
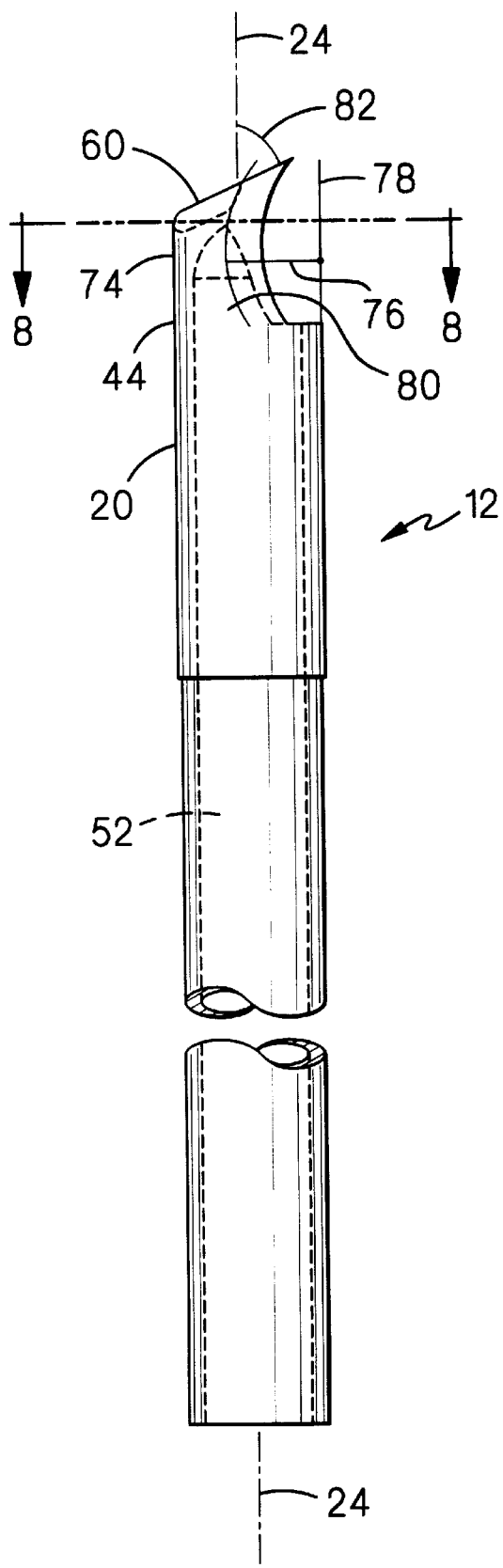
FIG. 5 is a side view of an inner tube of the surgical cutting instrument shown in FIG. 1.

Referring to FIG. 5, inner member 12 includes an inner tube 20, the proximal end of which is connected to a drive shaft 22 (FIGS. 1 and 2). The inner tube 20 has, e.g., a length of 176.231 mm (6.873") including the length of a cutter 44 discussed below, an outer diameter of 3.436 mm (0.134"), and an inner diameter of 2.641 mm–2.718 mm (0.103'–0.106"). The inner tube 20 is inserted into the outer tube 16 so that both are coaxially disposed along a longitudinal axis 24. The inner tube 20 includes an internal passageway 52 that extends along the longitudinal axis 24 from the proximal to the distal end of the inner tube 20. The proximal end of the internal passageway 52 is connected to a suction source when the surgical cutting instrument 10 is in operation.

Figure 6:
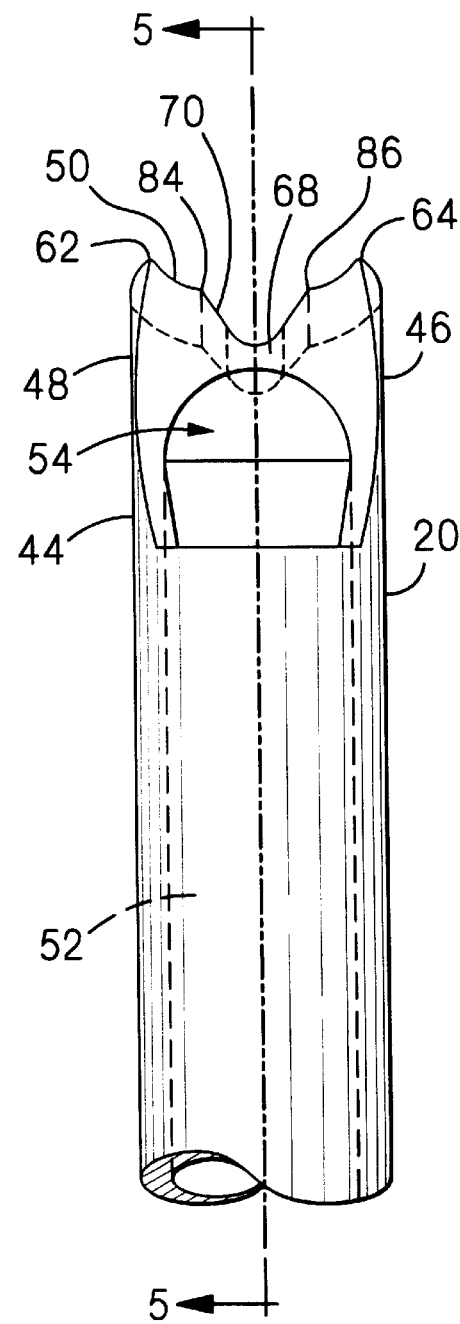
FIGS. 6-7 are front views of a distal region of the inner tube shown in FIG. 5.
Figure 7:
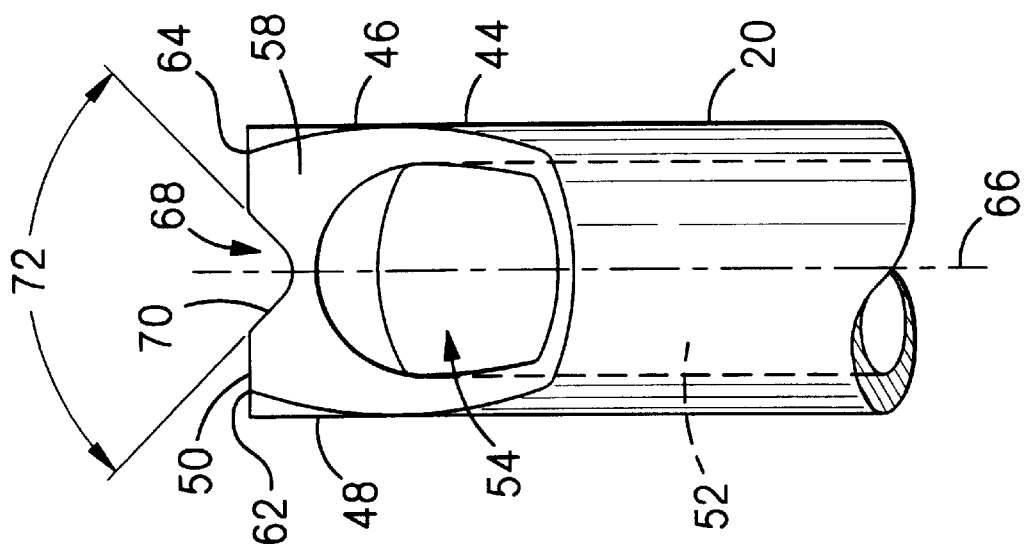

Referring to FIGS. 5–7, the cutter 44 is carried at the distal end of the inner tube 20. The outer diameter of the cutter 44 is larger than the outer diameter of the inner tube 20 to provide a closely toleranced fit with the inner diameter of the outer tube 16, e.g., 3.5692 mm–3.5820 mm (0.1392"–0.1397") The cutter 44 includes three cutting edges, a right-handed edge 46, a left-handed edge 48, and an upper edge 50. Lying in the U-shaped region defined by the three edges 46, 48, 50, an opening 54 is in fluid communication with the internal passageway 52 of the inner tube 20. The right-handed edge 46 is oriented in a clockwise direction along the outer circumference of the cutter 44, and the left-handed edge 48 is oriented in a counterclockwise direction along the outer circumference of the cutter 44. The upper edge 50 is located on the distal end of the cutter 44, and extends from the right-handed edge 46 to the left-handed edge 48. The three edges 46, 48, 50 are arranged symmetrically about a plane of symmetry 66 that extends along the longitudinal axis 24 and bisects the cutter 44.

The distal ends of the right-handed and left-handed edges 46, 48 terminate in two points. The right-handed edge 46 terminates at a right point 64 and the left-handed edge 48 terminates at a left point 62. The right point 64 is formed at the intersection of the right-handed edge 46 and the upper edge 50, and the left point 62 is formed at the intersection of the left-handed edge 48 and the upper edge 50. The right-handed and left-handed edges 46, 48 are "forward swept", i.e: the right point 64 projects in the clockwise direction, and the left point 62 projects in the counterclockwise direction.

Figure 8:
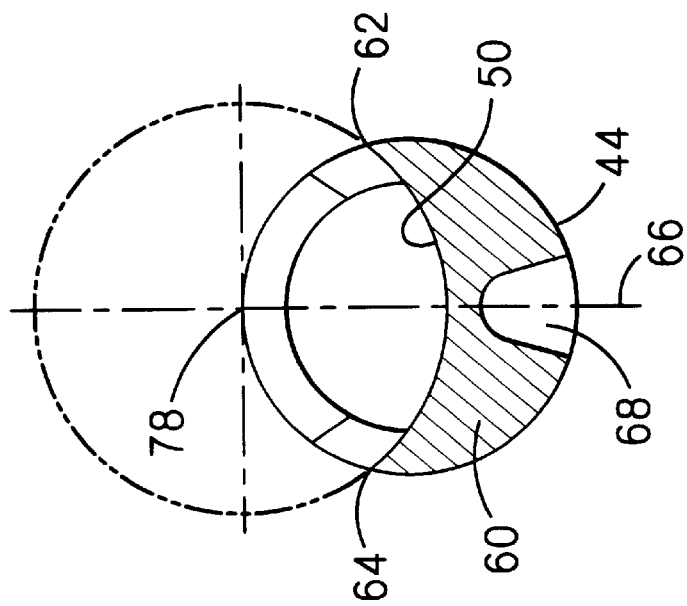
FIG. 8 is a sectional view of the inner tube taken through line 8—8 in FIG. 5.

Referring to FIGS. 5 and 8, the edges 46, 48, 50 and the opening 54 are formed by a revolved cut at the distal end of the inner tube 20, e.g., by electro-discharge machining (EDM) in which an electrode with a geometric shape is used to remove material from a closed-ended cutter "blank", i.e., a cup shaped metal item used to manufacture the cutter 44. The revolved cut is defined by a circular segment 80 that is rotated about a circumferential axis 78 that lies on the outer circumference of the cutter 44 and that extends parallel to the longitudinal axis 24. The plane of symmetry 66 is the plane defined by the circumferential axis 78 and the longitudinal axis 24. When viewed in a section taken along the plane of symmetry 66, the circular segment 80 has, e.g., a radius of 3.846 mm (0.150") that extends from an origin lying 1.615 mm (0.063") from the circumferential axis 78 in the plane of symmetry 66. The end points of the circular segment 80 define a chord that, e.g., has a length of 4.103 mm (0.160") and extends parallel to the longitudinal axis 24.

The revolved cut creates a revolved surface 58, shown in FIG. 7. The intersection of the revolved surface 58 and the outer circumference of the cutter 44 forms the right-handed edge 46 and the left-handed edge 48. The intersection of the revolved surface 58 and a planar area 60 located on the distal end of the cutter 44 forms the upper edge 50. As shown in FIG. 5, the planar area 60 lies at an angle 82 to axis 24 in the plane of symmetry 66. The angle 82 measures between approximately 30 degrees and 90 degrees, e.g., 65 degrees.

The cutter 44 has a solid region 74 of material that extends approximately 180 degrees around the outer circumference of the cutter 44 from the right-handed edge 46 to the left-handed edge 48. This solid and continuous region 74 provides circumferential support for the edges 46, 48 during cutting.

The cutter 44 further includes a notch 68, as shown in FIGS. 6 and 7. The notch 68 runs along the planar area 60 and is bisected by the plane of symmetry 66. The notch 68 intersects the planar area 60 forming two notch edges 70, 71. The notch edges 70, 71 are additional cutting edges that lie symmetrically, each on either side of and parallel to the plane of symmetry 66. The notch 68 forms, e.g., a curved surface with a radius from 0.513 mm–0.641 mm (0.020"–0.025"), measuring 1.462 mm–1.615 mm (0.057"–0.063") at its widest point, measuring 0.385 mm (0.015") in depth, and forming a notch angle 72 measuring 90 degrees.

When the inner tube 20 is inserted into the outer tube 16, the cutter 44 is positioned in close proximity to the tabs 26, 28. The right-handed and left-handed edges 46, 48 of the cutter 44 are periodically exposed through the side-facing openings 38, 40 as the inner tube 20 rotates relative to the outer tube 16 acting in conjunction with the cutting edges 30, 32, 34, 36 of the tabs 26, 28 to sever or shear tissue.

When the inner tube 20 is fully inserted, the distance from the left and right points 62 and 64 to the ends of the tabs 26, 28 is 0.513 mm (0.020"). This short distance is tolerable because the tabs 26, 28 do not have lips that extend over and cover the points of the cutting edges when viewed in the axial direction. The instrument 10 optionally utilizes a "blade lock" feature. When not rotating, the "blade lock" holds the edges 46, 48 in place against the tabs 26, 28 so that the cutter 44 is shielded and does not rotate as it is moved about the tissue. Therefore, when not rotating, the edges 46, 48 do not require "zeroing", i.e, the points 62, 64 do not need to be positioned underneath the lip to shield the edges 46, 48 and prevent rotation as the instrument 10 is moved within the tissue.

A lip requires an increase in the length of the tab so that the tab can be tapered from the lip to the desired width. The increased length as well as the lost exposure of the blade, which results from partially covering the blade with the lip, decreases the cutting ability of the blade. Because the distance between the points 62, 64 and the ends of the tabs 26, 28 can be reduced and because the cutting edges 46, 48 are not partially covered, cutting is improved, especially in the axial direction.

In operation, the cutter 44 can cut tissue in both directions of rotation: the right-handed edge 46 cuts tissue in cooperation with the left-handed cutting edges 30, 34 of the tabs when the cutter 44 rotates in a clockwise direction, and the left-handed edge 48 cuts tissue in cooperation with the right-handed cutting edges 32, 36 of the tabs when the cutter 44 rotates in a counterclockwise direction. Tissue is severed in a shearing motion caused by an edge 46, 48 of the cutter 44 moving closely past one of the cutting edges 30, 32, 34, 36 of the outer tube 16.

Because the left and right points 62, 64 are "forward swept", the points 62, 64 initiate the cut. The left point 62 initiates the cut in the counterclockwise direction, and the right point initiates the cut in the clockwise direction.

Tissue can be cut laterally or longitudinally (also known as axial boring) through the distal-end opening 42. The short distance from the ends of the tabs 26, 28 to the points 62, 64 aids the cutting, especially during axial boring.

The structure of the cutter 44, with the edges 46, 48, 50 oriented around a single opening 54, allows the opening 54 to be large relative to the size of the blades. Thus, the surgical cutting instrument 10 is capable of removing both relatively large fragments of tissue as well as relatively high volumes of tissue and fluid when suction is applied to the distal end of internal passageway 52. In addition, because the cutter 44 contains only a single opening 54, the suction is not split between multiple openings.

Other embodiments are within the scope of the following claims.

For example, a revolved cut can be geometric shapes other than the shape used to form the revolved surface 58. Thus, the revolved cut can be, e.g., spherical, cylindrical, or ovoid. In addition, multiple revolved cuts could be made, thus forming an instrument 10 that has multiple sets of opposed right-handed and left-handed cutting edges. The cutting edges defined by the revolved cut can alternatively be asymmetrical. The revolved surface can be formed by techniques other than EDM, e.g., metal injection molding.

One or more of the cutting edges 30, 32, 34, 36, 46, 48, 50, 70 need not be smooth, but instead can be serrated.

The cutter also can have multiple openings similar to opening 54, oriented, e.g., along the solid region 74 or along the distal end in the planar area 60 to further facilitate the evacuation of severed tissue and fluid.

What is claimed is:

1. A surgical cutting instrument disposed generally along an axis, the cutting instrument comprising:
   a first member extending distally from a base and having distal and proximal ends, the first member being rotatable to transmit torque from the base to the distal end of the member;
   a cutter carried at the distal end of the first member, the cutter having a first cutting edge defined by a symmetrical revolved surface.

2. The surgical cutting instrument of claim 1 wherein the first cutting edge is oriented in a right-handed direction and wherein the symmetrical revolved surface further defines a second cutting edge oriented in a left-handed direction.

3. The surgical cutting instrument of claim 2 wherein the first and second cutting edges are forward-swept.

4. The surgical cutting instrument of claim 2 wherein the first and second cutting edges are symmetrical with respect to one another about a plane of symmetry.

5. The surgical cutting instrument of claim 2 wherein the cutter comprises an uninterrupted circumferential band extending from the first cutting edge to the second cutting edge.

6. The surgical cutting instrument of claim 2 wherein the first and second cutting edges terminate in first and second distal points.

7. The surgical cutting instrument of claim 6 wherein the distal end of the cutter includes a generally planar area that intersects the first and second cutting edges at the respective first and second distal points.

8. The surgical cutting instrument of claim 7 wherein an angle between the planar area and a longitudinal axis of the cutter is between 30 degrees and 90 degrees.

9. The surgical cutting instrument of claim 8 wherein an angle between the planar area and a longitudinal axis of the cutter is between 30 degrees and 75 degrees.

10. The surgical cutting instrument of claim 9 wherein the angle is approximately 65 degrees.

11. The surgical cutting instrument of claim 7 wherein the generally planar area includes a notch.

12. The surgical cutting instrument of claim 2 further comprising a relatively rigid hollow second member coaxially disposed around the first member, the second member having a proximal end and a distal end and the first member being rotatable within the second member.

13. The surgical cutting instrument of claim 12 wherein the second member defines a first opening extending along a longitudinal axis of the second member and corresponding to the location of the cutter.

14. The surgical cutting instrument of claim 13 wherein the first opening is defined by an opposed pair of right-handed and left-handed cutting edges.

15. The surgical cutting instrument of claim 14 wherein the first cutting edge moves towards and closely past the left-handed edge of the first opening as the first member rotates clockwise with respect to the second member.

16. The surgical cutting instrument of claim 14 wherein the second cutting edge moves closely past the right-handed edge of the first opening as the first member rotates counterclockwise with respect to the second member.

17. The surgical cutting instrument of claim 13 wherein the second member defines a second opening extending along the longitudinal axis of the second member and corresponding to the location of the cutter.

18. The surgical cutting instrument of claim 12 wherein the distal end of the second member is substantially entirely open to expose a distal end of the cutter.

19. The surgical cutting instrument of claim 18 wherein the distal end of the second member terminates in a pair of longitudinally extending tabs, wherein longitudinal edges of the tabs define first and second openings extending along a longitudinal axis of the second member and corresponding to the location of the cutter.

20. The surgical cutting instrument of claim 1 wherein the first member defines an internal passageway in fluid communication with an opening defined in the cutter.

21. A surgical cutting instrument comprising:
   a first member extending distally from a base along an axis and having distal and proximal ends, the first member being rotatable to transmit torque from the base to the distal end of the member;
   a cutter carried at the distal end of the first member, the cutter having distal and proximal ends and defining a first cutting edge oriented in a right-handed direction and a second cutting edge oriented in a left-handed direction; and
   the distal end of the cutter defining a generally planar area that lies at an acute angle to the axis of the first member, the generally planar area intersecting the first and second cutting edges at respective first and second points.

22. The surgical cutting instrument of claim 21 wherein the angle between the generally planar area and the axis of the first member is between 30 degrees and 75 degrees.

23. The surgical cutting instrument of claim 22 wherein the angle is approximately 65 degrees.

24. The surgical cutting instrument of claim 21 wherein the generally planar area includes a notch.

25. The surgical cutting instrument of claim 21 wherein the first and second cutting edges are forward swept.

26. A surgical cutting instrument disposed generally along an axis, the cutting instrument comprising:
   a first member extending distally from a base and having distal and proximal ends, the first member being rotatable to transmit torque from the base to the distal end of the member;
   a cutter carried at the distal end of the first member, the cutter defining a first cutting edge oriented in a right-handed direction and a second cutting edge oriented in a left-handed direction, the first and second cutting edges being forward-swept;

a relatively rigid hollow second member coaxially disposed around the first member, the first member being rotatable within the second member and a distal end of the second member being substantially entirely open to expose a distal end of the cutter.

27. The surgical cutting instrument of claim 26 wherein the first and second cutting edges are symmetrical with respect to each other about a plane of symmetry.

28. The surgical cutting instrument of claim 26 wherein the first and second cutting edges terminate in first and second distal points.

29. The surgical cutting instrument of claim 28 wherein the distal end of the cutter includes a generally planar area that intersects the first and second cutting edges at the respective first and second distal points.

30. The surgical cutting instrument of claim 29 wherein an angle between the planar area and a longitudinal axis of the cutter is between 30 degrees and 90 degrees.

31. The surgical cutting instrument of claim 30 wherein an angle between the planar area and a longitudinal axis of the cutter is between 30 degrees and 75 degrees.

32. The surgical cutting instrument of claim 31 wherein the angle is approximately 65 degrees.

33. The surgical cutting instrument of claim 1 wherein the cutter is rotatable about a longitudinal axis of the cutter.

34. The surgical cutting instrument of claim 2 wherein the cutter is rotatable about a longitudinal axis of the cutter in the left-handed and the right-handed directions.

35. The surgical cutting instrument of claim 3 wherein the cutter is rotatable in first and second directions about a longitudinal axis of the cutter, the first and second cutting edges being forward-swept in the first and second directions, respectively.

36. The surgical cutting instrument of claim 4 wherein the cutter is rotatable about a longitudinal axis of the cutter, the longitudinal axis lying in the plane of symmetry.

37. The surgical cutting instrument of claim 21 wherein the cutter is rotatable about a longitudinal axis of the cutter in the left-handed and the right-handed directions.

38. The surgical cutting instrument of claim 26 wherein the cutter is rotatable in first and second directions about a longitudinal axis of the cutter, the first and second cutting edges being forward-swept in the first and second directions, respectively.

39. The surgical cutting instrument of claim 27 wherein the cutter is rotatable about a longitudinal axis of the cutter, the longitudinal axis lying in the plane of symmetry.

* * * * *